US006110740A

United States Patent [19]
Rome et al.

[11] Patent Number: 6,110,740
[45] Date of Patent: Aug. 29, 2000

[54] HUMAN VAULT RNA

[75] Inventors: Leonard H. Rome, Tarzana; Valerie A. Kickhoefer, Sherman Oaks, both of Calif.

[73] Assignee: Regents of the University of California, Oakland, Calif.

[21] Appl. No.: 09/276,975

[22] Filed: Mar. 26, 1999

Related U.S. Application Data

[60] Provisional application No. 60/079,634, Mar. 27, 1998.
[51] Int. Cl.$^7$ ........................... C07H 21/02; C07H 21/04; C12N 15/63; C12N 15/85; C12Q 1/68
[52] U.S. Cl. ........................... 435/325; 435/6; 435/91.1; 435/252.3; 435/320.1; 536/23.1; 536/23.51; 536/24.3; 536/24.31; 536/24.33
[58] Field of Search ........................... 435/6, 91.1, 440, 435/375, 325; 536/23.1, 23.2, 29.5, 24.3; 514/44

[56] References Cited

FOREIGN PATENT DOCUMENTS

WO 96 27611A  9/1996  WIPO .

OTHER PUBLICATIONS

Andrea D. Branch, A good antisense molecule is hard to find, TIBS, 47–48, Feb. 1998.

Trisha Gura, Antisense Has Growing Pains, Science, pp. 575–577, Oct. 1995.

Stanley Crooke, Antisense '97: A roundtable on the state of the Industry, Nature Biotechnology, p. 522, Jun. 1997.

Stanley Crooke, Antisense Research and Applications, Chapter 1, Basic Principles of Antisense Therapeutics, Springer–Verlag Press, Berlin, Heidelberg, New York, p. 3, Jul. 1998.

Chugani, Diane C. et al. Evidence that vault ribonucleoprotein particles localize to the nuclear pore complex. *Journal of Cell Science*, 1993, 106:23–29.

George, David G. et al. Current Methods in Sequence Comparison and Analysis. *Macromolecular Sequencing and Synthesis Selected Methods and Applications*, 1988, pp. 127–149, Alan R. Liss, Inc., New York.

Kickhoefer, Valerie A. et al. Vaults Are Up–regulated in Multidrug–resistant Cancer Cell Lines. *J. Biol. Chem.* 273:8971–8974, Apr. 1998.

Kickhoefer, Valeria A. et al. Vault Ribonucleoprotein Particles from Rat and Bullfrog Contain a Related Small RNA That is Transcribed by RNA Polymerase III. *The Journal of Biological Chemistry*, Apr. 1993, vol. 268, No. 11, pp. 7868–7873.

Rome, Leonard H. Multidrug resistance: Locked in the vault? *Nature Medicine*, 1995, vol. 1, No. 6, p. 527.

Rome, Leonard et al. Unlocking vaults: organielles in search of a function. *Trends in Cell Biology*, 1991, vol. 1, No. 213, pp. 47–50.

Scheffer, George L. et al. The drug resistance–related protein LRP is the human major vault protein. *Nature Medicine*, 1995, vol. 1, No. 6, pp. 578–582.

Mart. S.M. et al., "Expression of the human major vault protein LRP in acute myeloid leukemia", *Experimental Hematology*, 25(12):1227–1232, Nov. 1997.

Irman, E.M. et al., "Targeted Degradation of the Vault RNA (vRNA) in vivo Using Antisense Oligodeoxynucleotides," *Molecular Biology of the Cell*, vol. 6, Suppl., p. 196a, 1995.

Izquierdo, M.A. et al., "Relationship of LRP–human major vault protein to in vitro and clinical resisttance to anticancer drugs," *Cytotechnology*, 19(3):191–197, 1996.

Kickhoefer, V.A. et al., "Multidrug resistant cancer cell lines contain elevated levels of vaults," *Proceedings of the American Association for Cancer Research Annual Meeting*, 38:252, 1997.

Kickhoefer, V.A. et al., "Vaults are the answer, what is the question?," *Trends in Cell Biology*, 6(5):174–178 1996.

*Primary Examiner*—George C. Elliott
*Assistant Examiner*—Janet Epps
*Attorney, Agent, or Firm*—David A. Farah; Sheldon & Mak

[57] ABSTRACT

A polynucleotide encoding a human vault-associated vRNA or its complementary strand. A purified and isolated polynucleotide molecule consisting essentially of a human vault RNA, or its complementary strands, or a combination of a nucleotide sequence consisting essentially of a human vault RNA and its complementary strands. A method of diagnosing a patient with a multidrug-resistant cancer. A method of treating a patient with multidrug-resistant cancer. A composition for treating multidrug-resistant cancer comprising a polynucleotide which hybridizes with a human vault-associated vRNA. A method of screening for compositions for treating a patient with multidrug-resistant cancer.

20 Claims, 9 Drawing Sheets

```
              10         20         30         40         50
              •          •          •          •          •
hvg1  GGCTGGCTTTAGCTCAGCGGTTACTTCGACAGTTCTTTAATTGAAACAAG
hvg2  ------------------------------GTACAT-G---CC********
hvg3  ------------------------------CGTG-CA-CA--CC********

60         70         80         90
              •          •          •          •
hvg1  CAACCTGTCTGGGTTGTTCGAGACCCGCGGGCGCTCTCCAGTCCTTTT
hvg2  **----C--------G------------------T---T-----CT-----
hvg3  **----C----------------------------------C---C--
```

HUMAN VAULT RNA

CROSS-REFERENCE TO RELATED APPLICATION

This application claims priority under 35 U.S.C. 119(e) to provisional U.S. patent application Ser. No. 60/079,634, entitled "Human Vault RNA," filed Mar. 27, 1998.

STATEMENT REGARDING FEDERALLY SPONSORED RESEARCH OR DEVELOPMENT

The present invention was made with government support under Grant No. GM 38097, awarded by the National Institutes of Health. The United States Government has certain rights in this invention. BACKGROUND Cancer is a major cause of morbidity and mortality in the United States. Treatment of cancer generally includes chemotherapy, radiation therapy and surgery. Unfortunately, most cancers cannot be cured using chemotherapy because tumor cells tend to develop resistance to several chemotherapeutic agents over time. These cancers are referred to as "multidrug-resistant cancers" (MDR).

Overexpression of a number of proteins has been found to be associated with MDR cells lines, including P-glycoprotein (Pgp) and multidrug resistance-associated protein (MRP). These proteins appear to mediate drug resistance by acting as cytotoxic drug efflux pumps. However, many MDR cancer cell lines are known which are not associated with overexpression of either P-glycoprotein or multidrug resistance-associated protein.

More recently, a protein has been described that is overexpressed in MDR tumor cell lines which do not overexpress either P-glycoprotein or multidrug resistance-associated protein. This protein was originally named Lung Resistance-related Protein (LRP), referring to the cell line in which it was originally identified. However, once the cDNA for Lung Resistance-related Protein was isolated and the corresponding protein sequence elucidated, it was found that Lung Resistance-related Protein was human major vault protein (MVP), a previously known protein.

Vaults are large, barrel-shaped, multi-subunit, cytoplasmic, ribonucleoprotein organelles found in virtually all higher organisms and in most normal tissues. Mammalian vaults consist of three proteins 240, and a small RNA (vRNA) in the relative molar ratios of 1:1:24:4 in rats. The human vault RNA has not yet been characterized.

MVP has been shown to be overexpressed in many non-Pgp MDR tumor cell lines, including the SW1573/2R120 (non-small cell lung cancer), GLC4/ADR (small cell lung cancer), MCF-7/MR (breast cancer), and 8226/MR20 (myeloma) cell lines. Furthermore, revertant cell lines, which were isolated by culturing in the absence of drug, down-regulate the expression of MVP. However, transfection studies have shown that overexpression of the MVP cDNA alone is not sufficient to confer a drug resistant phenotype.

Therefore, there remains a need for agents that will target multidrug-resistant cancers. Further, there remains a need for a method for treating multidrug-resistant cancers. Additionally, there remains a need to characterize the human vault RNA.

SUMMARY

According to one embodiment of the present invention, there is provided a polynucleotide encoding a human vault-associated vRNA, including a polynucleotide having a sequence as set forth in SEQ ID NO:1, SEQ ID NO:2, SEQ ID NO:3, or their complementary strands. According to another embodiment of the present invention, there is provided a purified and isolated polynucleotide molecule having a sequence as set forth in SEQ ID NO:4, or its complementary strands.

According to another embodiment of the present invention, there is provided a purified and isolated polynucleotide molecule consisting essentially of a human vault vRNA, or its complementary strands, or a combination of a nucleotide sequence consisting essentially of a human vault vRNA and its complementary strands.

According to yet another embodiment of the present invention, there is provided a method of diagnosing a patient with a multidrug-resistant cancer comprising, first providing a sample of tissue or fluid from the patient and determining the level of a human vault-associated vRNA in the patient sample. Then, the level of the human vault-associated vRNA determined is compared to a known range of levels for the human vault-associated vRNA in patients with multidrug-resistant cancers. A diagnosis of multidrug-resistant cancer is made when the level of the human vault-associated vRNA determined is within the range of levels for the human vault-associated vRNA in patients with multidrug-resistant cancers.

According to another embodiment of the present invention, there is provided a method of diagnosing a patient with a multidrug-resistant cancer comprising, first, providing a sample of tissue or fluid from the patient and determining the level of vaults in the patient sample. Then, the level of vaults determined is compared to a known range of levels for the vaults in patients with multidrug-resistant cancers. A diagnosis of multidrug-resistant cancer is made when the level of the vaults determined is within the range of levels for the vaults in patients with multidrug-resistant cancers.

According to yet another embodiment of the present invention, there is provided a method of treating a patient with multidrug-resistant cancer comprising diagnosing a patient with multidrug-resistant cancer according to the method disclosed herein and then treating the patient. The treatment can comprise administering to the patient a polynucleotide which hybridizes with a human vault-associated vRNA, such as a polynucleotide selected from the group consisting of a sequence complimentary to residues 21–38 of SEQ ID NO:1, complimentary to residues 39–53 of SEQ ID NO:1, and complimentary to residues 50–65 of SEQ ID NO:1.

Additionally, another embodiment of the invention is a composition for treating a patient with multidrug-resistant cancer comprising a polynucleotide which hybridizes with a human vault-associated vRNA. The polynucleotide can have a sequence complimentary to residues 21–38 of SEQ ID NO:1, or can have a sequence complimentary to residues 39–53 of SEQ ID NO:1, or can have a sequence complimentary to residues 50–65 of SEQ ID NO:1, or can have a combination of these foregoing sequences.

Further, there is provided a method of screening for compositions for treating a patient with multidrug-resistant cancer. The method comprises determining compositions or treatments that disrupt the association of vRNA with vault particles. In a preferred embodiment, the compositions or treatments determined disrupt the association of vRNA with the minor vault proteins of vault particles.

FIGURES

These and other features, aspects and advantages of the present invention will become better understood with regard to the following description, appended claims, and accompanying figures where:

DESCRIPTION

The present invention involves the elucidation of the nucleotide sequences of human vault RNAs (vRNA) and the nucleotide sequences encoding human vault RNAs (hvg). Additionally, the relationship between vault numbers and multi-drug resistant phenotype is determined. These sequences and this relationship are then utilized in the preparation of compositions for the treatment of multidrug resistance cancer, in methods of diagnosing multidrug resistance cancer, and in methods of treating multidrug resistance cancer.

A) Determination and Characterization of the Human Vault RNA sequences and the Nucleotide Sequences Encoding Human Vault RNA:

The human vault RNA sequences and the nucleotide sequences encoding the human vault RNAs were determined as follows. First, the genes encoding the human vault RNAs were isolated by screening a Lambda FIX II (Stratagene, San Diego, Calif., US) human genomic DNA library. A total of $6.25 \times 10^5$ recombinants were screened according to techniques described in Kickhoefer, V. A. et al. (1993) *J. Biol. Chem.* 268, 7868–7873, incorporated herein by reference in its entirety, using a random primed partial human vRNA gene. Comparisons between the rat and bullfrog vRNA sequences revealed that bases 11–27 and 110–129 (based on the rat vRNA Sequence GenBank accession no. 21171) were conserved. Primers to these conserved regions were synthesized on an Applied Biosystems DNA synthesizer and used to polymerase chain reaction partial human vRNA genes from genomic DNA. The purified polymerase chain reaction products were subcloned into pBluescript SK+(Stratagene) and sequenced by the dideoxy method using Sequenase (U.S. Biochemical Corp.). These partial human vRNA genes were used as hybridization probes.

Two clones, nos. 1 and 4, were identified and plaque-purified. Based on Southern blot analysis, a 350-base Sac1 fragment was subcloned into pBluescript SK+ and sequenced, yielding a sequence designated hvg1, SEQ ID NO:1. Subcloning and sequence analysis revealed that the second clone (no. 4) contained two vRNA genes, designated hvg2, SEQ ID NO:2, and designated hvg3, SEQ ID NO:3, within about 7 kilobase pairs of each other. The sequences were submitted to GenBank™ and given accession nos. AF045143, AF045144, and AF045145, respectively, for hvg1, hvg 2 and hvg 3. Using these sequences, a search of the GenBank™ database was performed for related sequences and one additional member of the human vRNA gene family was identified on chromosome X, accession bases 58392 to 58492 of number Z97054, which we designated hvg4. The sequences of the four genes encoding these four human vRNAs are as follows:

SEQ ID NO:1 (AF045143, hvg1):
  GGCTGGCTTTAGCTCAGCGGTTACTTC-
  GACAGTTCTTTAATTGAAACAAG CAACCT-
  GTCTGGGTTGTTCGAGAC-
  CCGCGGGCGCTCTCCAGTCCTTTT SEQ ID NO:2 (AF045144, hvg2):
  GGCTGGCTTTAGCTCAGCGGTTACTTC-
  GAGTACATTGTAACCACCTCTCT GGGTGGTTC-
  GAGACCCGCGGGTGCTTTCCAGCTCTTTT SEQ ID NO:3 (AF045145, hvg3)
  GGCTGGCTTTAGCTCAGCGGTTACT-
  TCGCGTGTCATCAAACCACCTCTCT GGGTTGT-
  TCGAGACCCGCGGGCGCTCTCCAGCCCTCTT SEQ ID NO:4 (bases 58392 to 58492 of Z97054, hvg4)
  GGCTGGCTTTAGCTCAGCGGTTACTTC-
  GACAATGCTTTCCATGGTTAGGA AACCAAC-
  CTCTCTGGGTGGTTTGAGACCCGTGGGC-
  CCTCTCCAGTCCTTTT The four human vRNAs, hvg1 vRNA, hvg2 vRNA, hvg3 vRNA and hvg4 vRNA, have the complementary sequences to their respective encoding genes.

Figure 1:
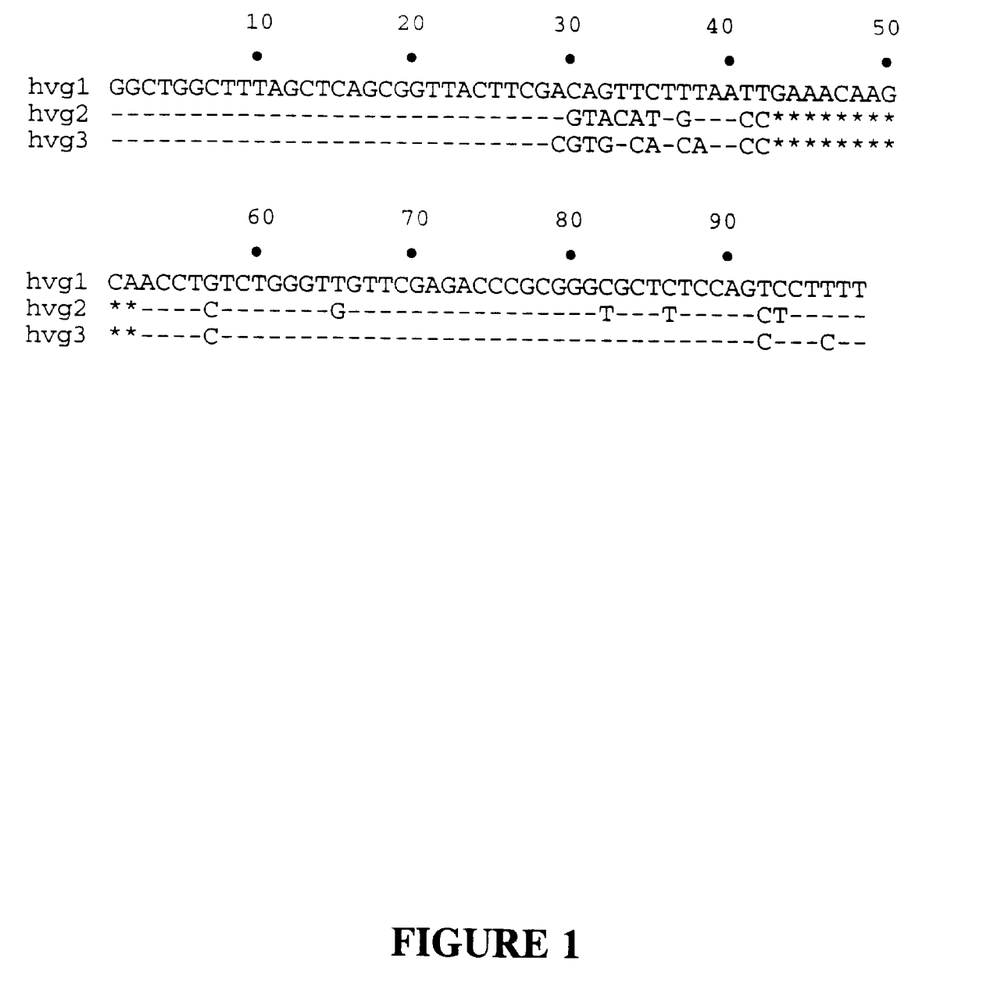
FIG. 1 shows a comparison of hvg1, hvg2 and hvg3, where identical bases are indicated by dashes and deletions are indicated by asterisks.

Referring now to FIG. 1, there is shown a comparison of hvg1, hvg2, and hvg3. Identical bases are indicated by dashes. Asterisks indicate a deletion. As can be seen, hvg1 is 96 bases in length while hvg2 and hvg3 are 88 bases in length. Further, hvg1, hvg2 and hvg3 share about 84% identity with each other. All three human vRNA genes contain internal RNA polymerase n-type promoter elements located at bases 11–20 and bases 65–75, respectively, based on the hvg1 sequence.

B) Determination of Human vRNA Levels in Non-Pgp Multiple Drug-Resistant Cell Lines:

Next, the level of human vRNA was determined in several non-Pgp multi drug-resistant cell lines. First, several multiple drug resistant cell lines were maintained as follows. SW1573/2R120 (non-small cell lung cancer), and GLC4/ADR (small cell lung cancer) were cultured in the presence of 115 and 1156 nM doxorubicin, respectively, one time per week. Similarly, MCF-7/MR (breast cancer cells) and 8226/MR4, 8226120 (myeloma cells) were cultured in the presence of 80, 40, and 200 nM mitoxanthrone, respectively, two times per week. Drug-sensitive SW1573, GLC4/S, MDF-7, and 8226/S cells were grown in RPMI 1640 medium which was supplemented with 10% fetal bovine serum and antibiotics.

Then, extracts were prepared by subcellular fractionation of various drug-sensitive, drug-resistant, and drug-revertant cell lines as follows. $1 \times 10^8$ cells were harvested, counted, and resuspended in 5 ml of cold buffer A (50 mM Tris-Cl (pH 7.4), 1.5 mM $MgCl_2$ and 75 mM NaCl) containing 0.5%

Nonidet P40, 1 mM phenylmethylsulfonyl fluoride, and protease inhibitor mixture (2 µg/ml aprotinin, 0.5 mM benzamidine, 2 mg/ml chymostatin, 5 µM leupeptin, 5 µM pepstatin). All subsequent steps were performed at 4° C. Cells were vortexed, incubated on ice for 5 minutes and centrifuged at 20,000×g for 20 minutes The postnuclear supernatant fraction was centrifuged at 100,000×g for 1 hour. The resulting supernatant was designated the S100 fraction. The nuclear pellets, the N fraction, and the 100,000×g pellets, the P100 fraction, were resuspended by Dounce homogenization in buffer A containing 10% glycerol, 1 mM phenylmethylsulfonyl fluoride, and protease inhibitors in the original volume. Equal volume amounts of fractions were analyzed for protein and RNA content. The GLC4/ADR P100 fraction was then applied to a 20/30/40/45/50/60% sucrose step gradient in buffer A (containing L/2/2/2/2/1 ml in each layer, respectively) and centrifuged at 28,000 rpm in a Beckman SW-41 rotor for 16 hours. Under these conditions, intact vault particles localize to the 40/45% sucrose layers. Gradient fractions for each layer were collected, diluted 4-fold with buffer A, and centrifuged for 3 hours at 100,000×g. Pellets were resuspended in buffer A and analyzed for both protein and RNA content.

Then, protein samples were solubilized in SDS sample loading buffer, fractionated on 7.5% SDS-polyacrylamide gel electrophoresis, and transferred to Hybond-C (Amersham Corp.) by electroblotting. Western blots were performed using the anti-rat vault polyclonal antibody (N2) following established procedures. Reactive bands were detected using the enhanced chemiluminescence system (Amersham Corp.). RNA from cellular fractions were purified by pheno/chloroform extraction and ethanol precipitation. Total RNA was isolated by the guanidinium-phenol method. Subsequently, the RNAs were fractionated by 8 M urea, 10% polyacrylamide gels, and electroblotted to Zeta GT membrane (Bio-Rad). The membrane was hybridized with a randomly primed human vRNA gene probe (hvg1, specific activity $1\times10^9$ cpm/µg). Hybridization was carried out according to the manufacturer's recommendation. Hybridized bands were detected by autoradiography. Quantitation of reactive bands (either protein or RNA) was carried out by scanning with a Molecular dynamics personal densitometer SI using ImageQuant software. Fold changes in Table I were calculated from multiple data sets, except for the GLC4 data set, which matched previously published values.

Using these subcellular fractionation techniques, vaults pellet at 100,000×g, the P100 fraction, and all of the MVP is associated with this fraction and is assembled into vaults. In contrast, only a portion of the total cellular vRNA fractionates to the P100 fraction where it is associated with vaults. This non-vault-associated vRNA fractionates in the soluble or S100 fraction.

Figure 2:
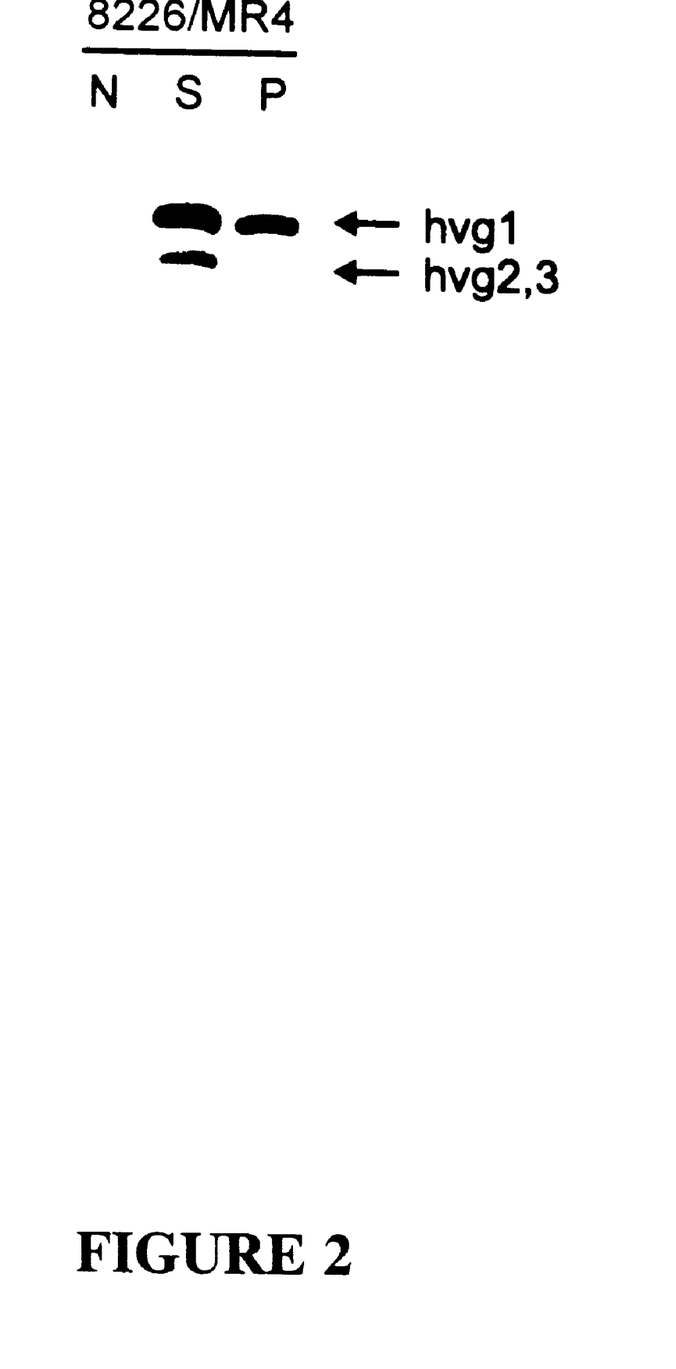
FIG. 2 shows a Northern blot of hvg1 vRNA, hvg2 vRNA and hvg3 vRNA in fractionated 8226/MR4 cells.

Referring now to FIG. 2, there is shown a Northern blot of hvg1 vRNA, hvg2 vRNA and hvg3 vRNA in fractionated 8226/MR4 cells. As can be seen, hvg1 vRNA is present in both the vault-associated P100 fraction and in the non-vault associated S100 fraction. By contrast, the hvg2 vRNA and the hvg3 vRNA are present in only the non-vault associated S100 fraction.

Figure 3:
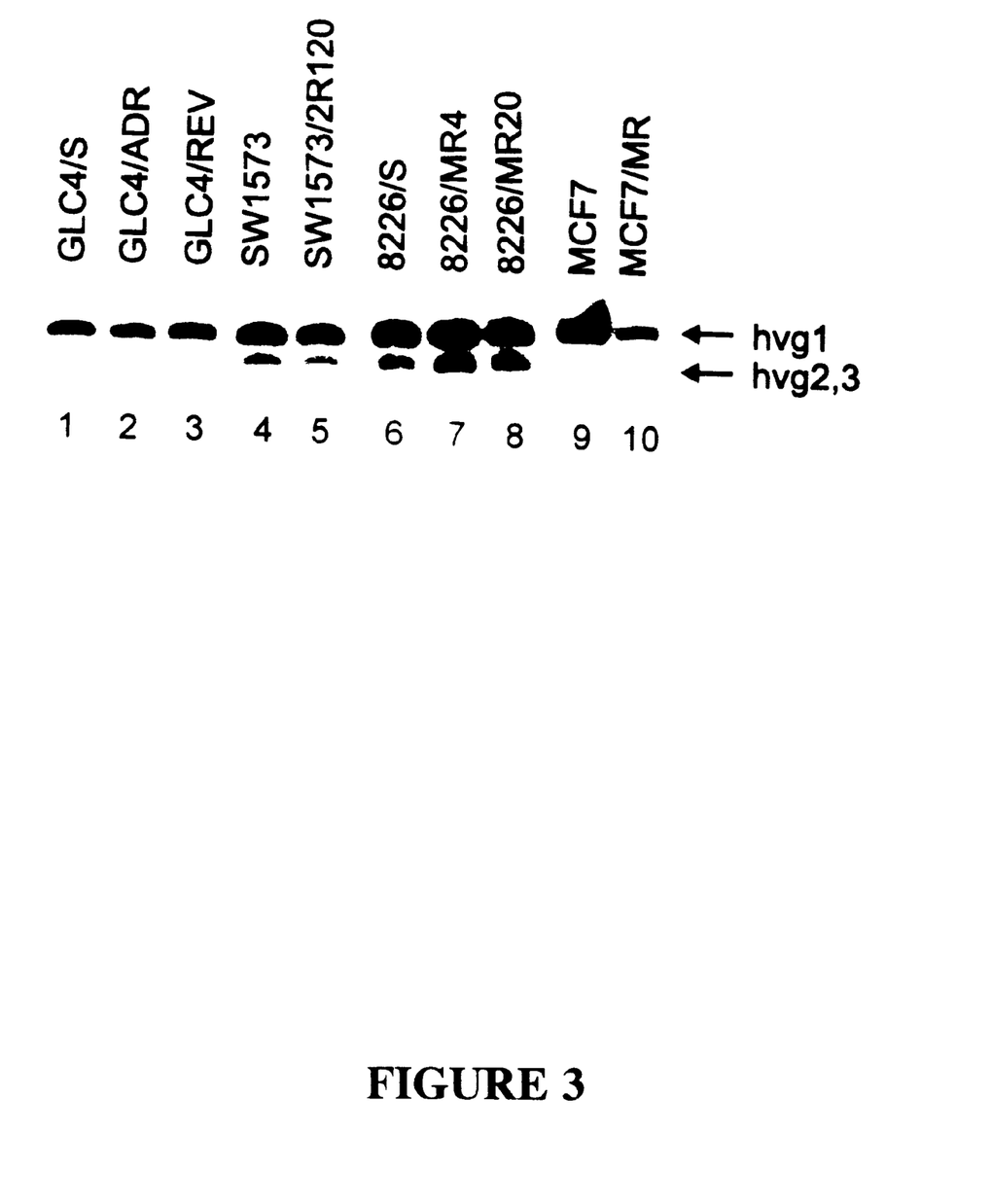
FIG. 3 shows a Northern blot of total hvg1 vRNA, hvg2 vRNA and hvg3 vRNA in several cell lines.

Referring now to FIG. 3, there is shown a Northern blot of total hvg1 vRNA, hvg2 vRNA and hvg3 vRNA in several cell lines. As can be seen, hvg1 vRNA is present in all tested cell lines, top lanes 1–10, while both hvg2 vRNA and hvg3 vRNA were present in only five of the 10 cell lines tested, bottom lanes 4–8.

Therefore, although there are multiple human vRNAs, we have determined that only the form encoded by hvg1 is consistently present in all cell lines and consistently associates with the vault particle as evidenced by pelting at 100,000×g. By contrast, the vRNAs encoded by hvg2 and hvg3 are not present in all of the cell lines and are not consistently associated with vaults, although they are associated with vaults in some cancer cell lines such as MDR HeLa cells, data not shown. However, PCR analysis of genomic DNA from these lines indicates the all three genes are uniformly present, data not shown.

C) Determination of Human Vault Levels in Non-Pgp Multiple Drug-resistant:

Next, the level of human vaults in the parental cell lines were determined by comparison of protein levels in the P100 fraction from $4\times10^8$ cells per lane to purified rat liver vaults (0.05, 0.10, 0.15, 0.20, and 0.25 µg). Western analysis and quantitation was carried out as described herein. A vault standard curve was generated and linear regression analysis was used to estimate the number of vault particles per cell in the parental cell lines. Values for the drug-resistant and drug-revertant cell lines were calculated using the fold changes determined in Table I.

Figure 4:
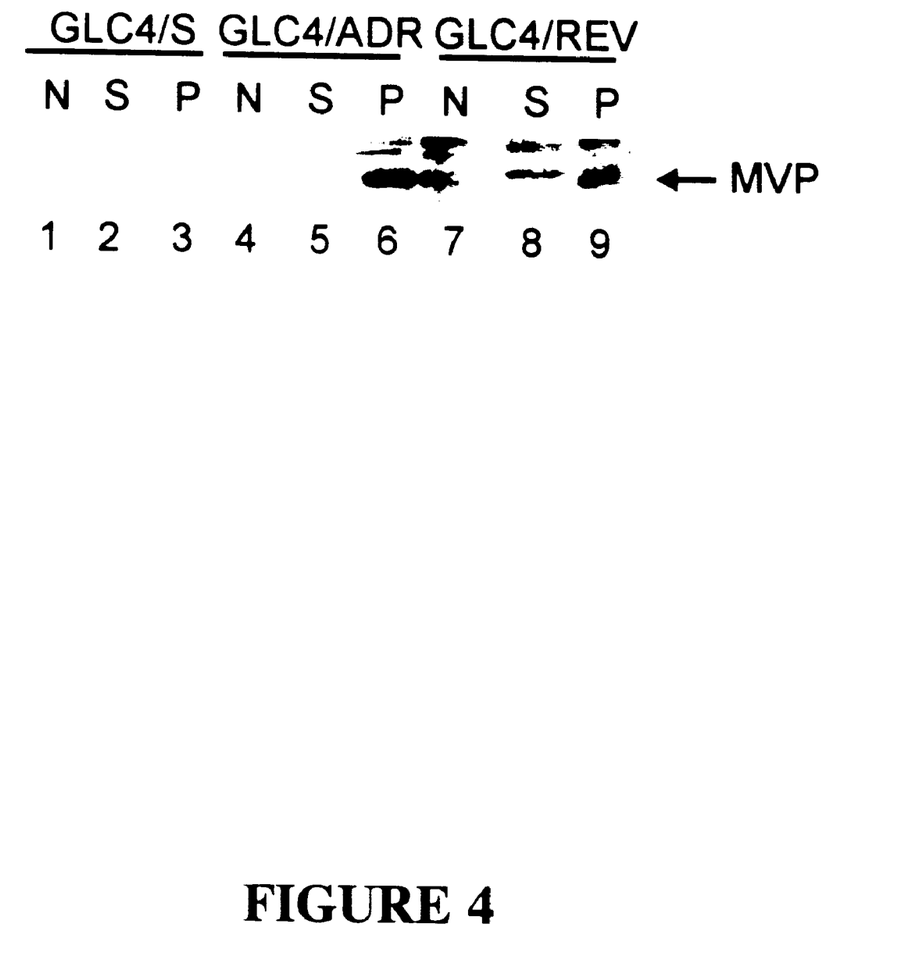
FIG. 4 shows a Western blot of MVP in fractionated small cell lung cancer cells GLC4/S (parental), and cells of its derivative drug-resistant cell line GLC4/ADR and cells of its derivative drug-revertant cell line GLC4/REV for the N fraction, P100 fraction and S100.

Referring now to FIG. 4, there is shown a Western blot of MVP in fractionated small cell lung cancer cells GLC4/S (parental), and cells of its derivative drug-resistant cell line GLC4/ADR and cells of its derivative drug-revertant cell line GLC4/REV for the N fraction, P100 fraction and S100. As can be seen, MVP is primarily associated with the P100 fraction of both the GLC4/ADR and the GLC4/REV cells, and MPV levels were less in the drug-revertant cell line as compared to the drug-resistant cell line, lanes 6 and 9.

Figure 5:
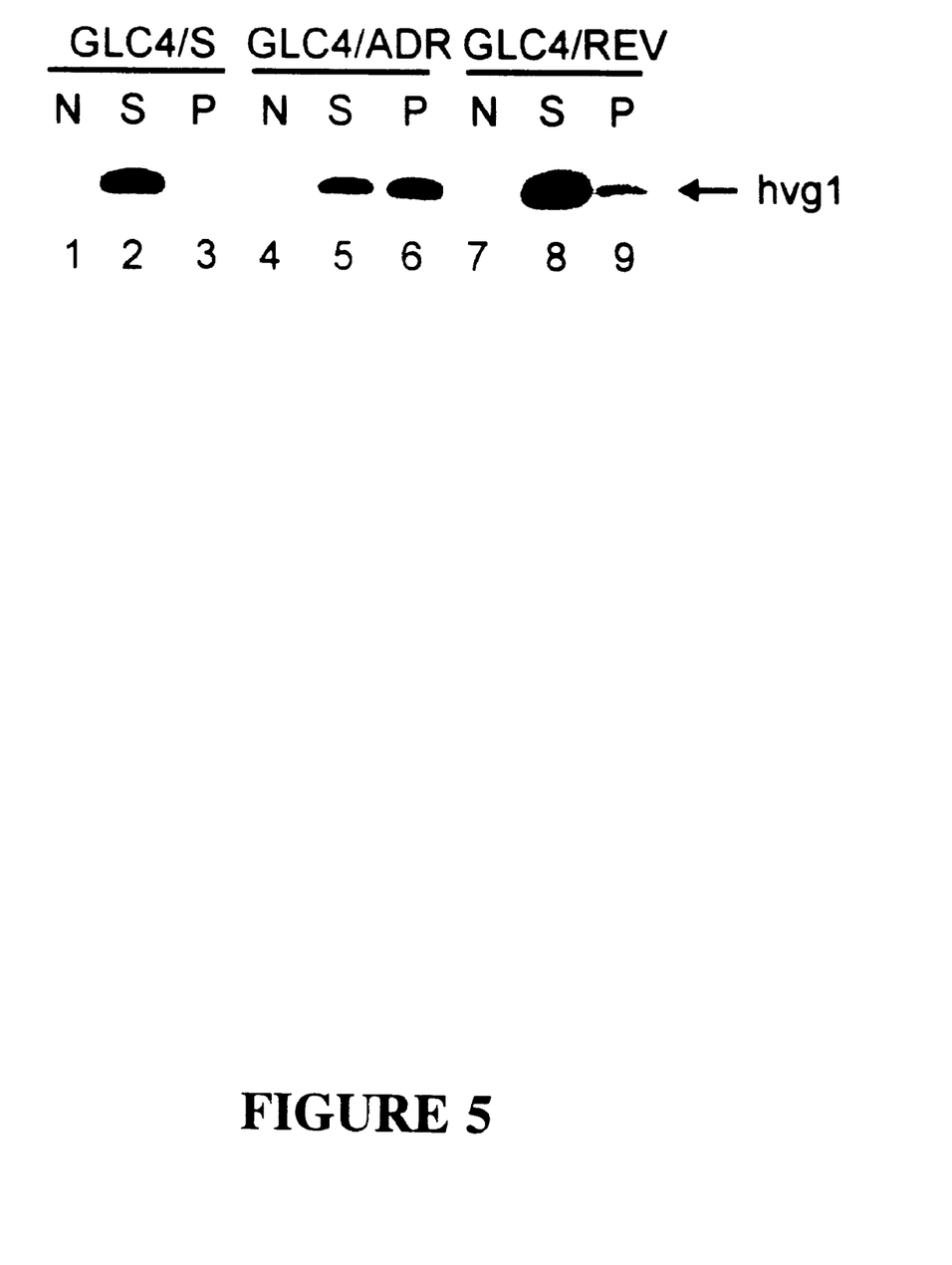
FIG. 5 shows a Northern blot of hvg1 RNA in fractionated small cell lung cancer cells GLC4/S, GLC4/ADR and GLC4/REV for the N fraction, P100 fraction and S100 extracted for RNA.

Referring now to FIG. 5, there is shown a Northern blot of hvg1 vRNA in fractionated small cell lung cancer cells GLC4/S, GLC4/ADR and GLC4/REV for the N fraction, P100 fraction and S100 extracted for RNA. As can be seen, vault-associated hvg1 vRNA increased about 15-fold, lanes 3 and 6, from the parental cell line to the drug-resistant cell line. Further, there was a shift in the presence of the hvg1 vRNA from the non-vault associated S100 fraction to the vault-associated P100 fraction in the drug-resistant line, lanes 5 and 6. This indicates that an increasing fraction of hvg1 vRNA is associated with vaults in the drug-resistant line than in the parental line. Similarly, vault-associated hvg1 vRNA levels were less in the drug-revertant cell line as compared to the drug-resistant cell line lanes 6 and 9. Further, both the MVP and hvg1 vRNA levels decrease to comparable levels in the drug-revertant cell line compared to the drug-resistant cell line (Table I).

Figure 6:
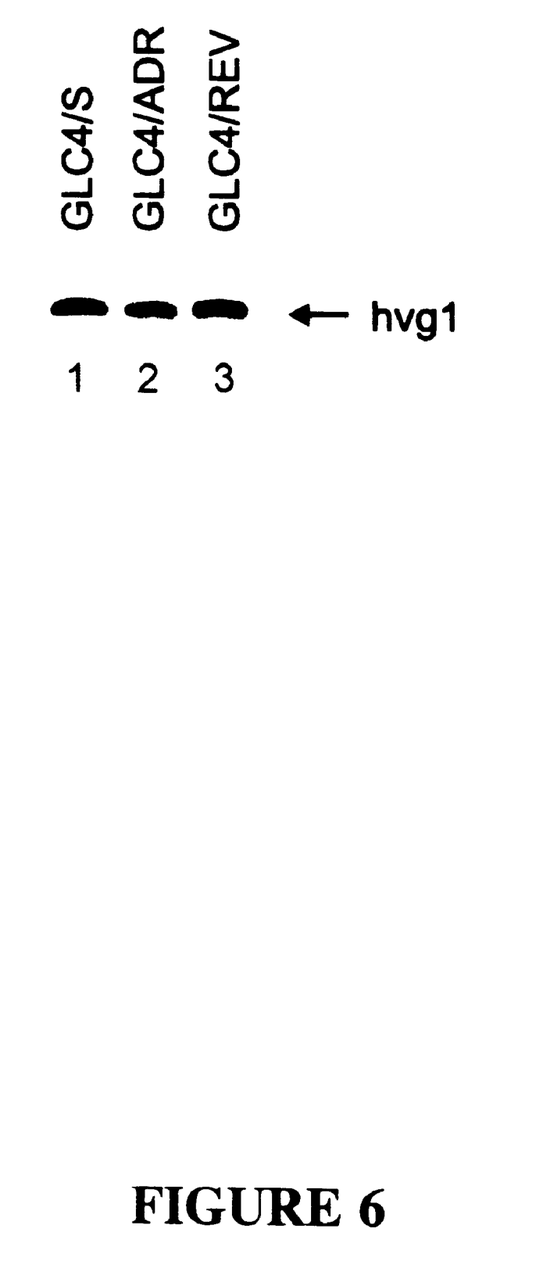
FIG. 6 shows a Northern blot of total hvg1 vRNA in 10 μg of small cell lung cancer cells GLC4/S, GLC4/ADR and GLC4/REV.

Referring now to FIG. 6, there is shown a Northern blot of total hvg1 vRNA in 10 µg of small cell lung cancer cells GLC4/S, GLC4/ADR and GLC4/REV. As can be seen, total vRNA levels remained constant in the three cell lines. Therefore, the increased association of vRNA with vaults in the drug-revertant and drug-resistant cell lines is not due to an increase in transcription of the vRNA gene. Further, only about 20% of the total vRNA is associated with the vault particle in these MDR cancer cell lines (data not shown). Thus, an increase in the total number of vault particles that occurs in the drug-resistant cell lines results in an increase in the vault-associated fraction of the total vRNA pool. Correspondingly, in the drug-revertant cell lines, there is a decrease in the vault-associated fraction of the total vRNA pool as compared to the drug-resistant cell lines, but an increase over parental cell lines. Additionally, UV crosslinking studies indicated that the vRNA interacts primarily with the minor vault proteins and not the MVP (data not shown).

Figure 7:
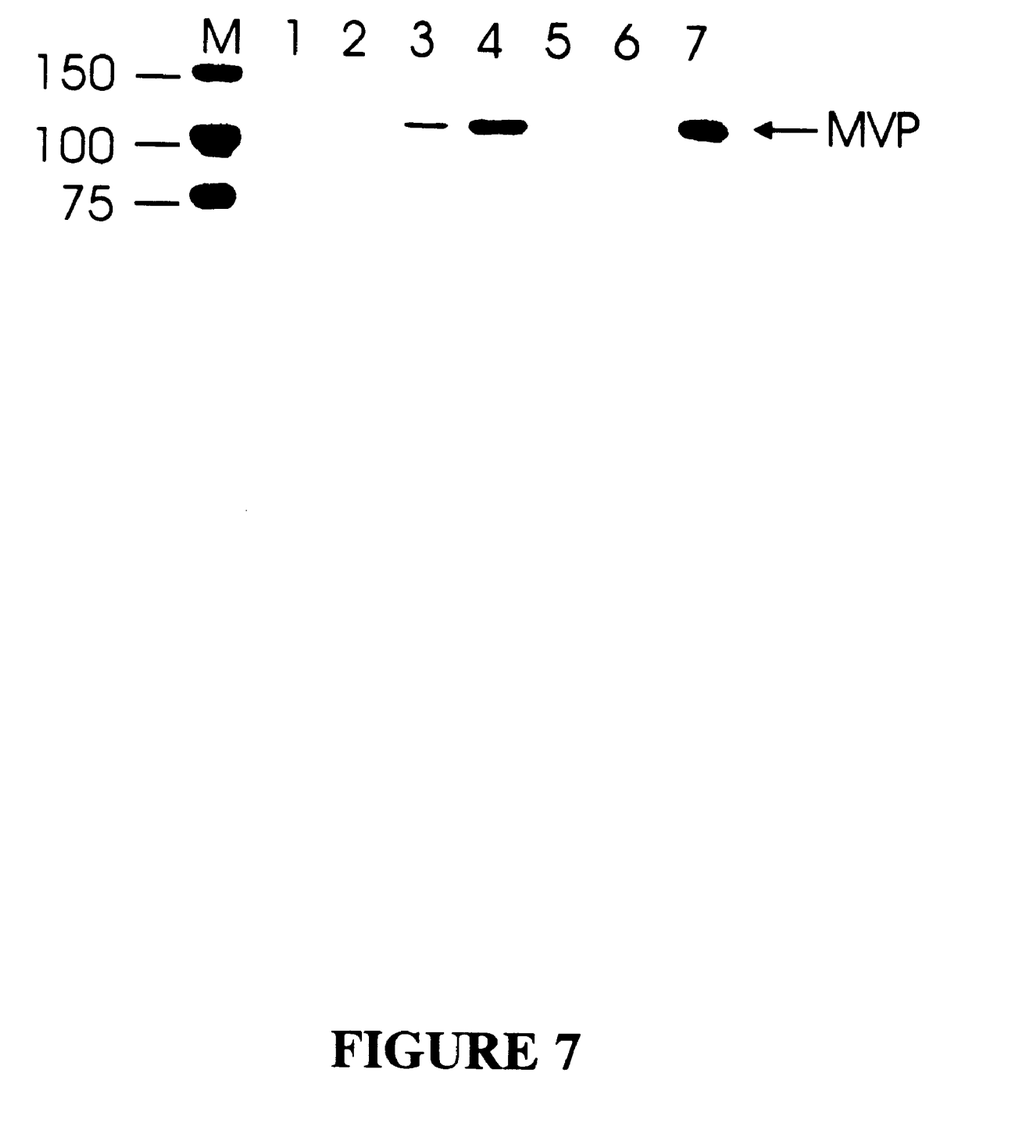
FIG. 7 shows a Western blot of MVP levels in a sucrose equilibrium gradient, where lane 1–6 correspond to the load 20, 30, 40, 45, 50 and 60% layers, respectively, and lane 7 corresponds to GLC/4/ADR P100 fraction layer.
Figure 8:
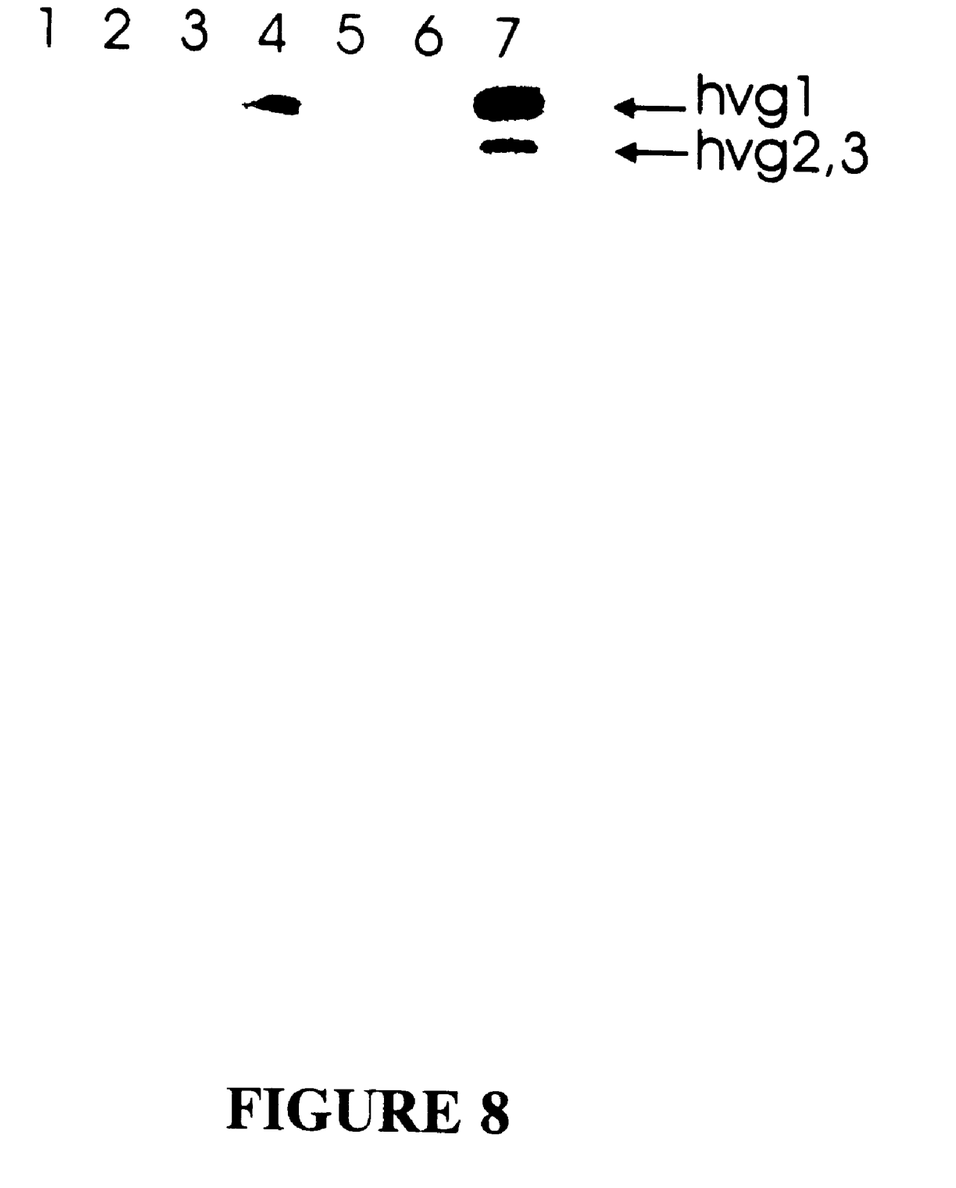
FIG. 8 shows a Northern blot of RNA extracted from gradient fractions of FIG. 7, lanes 1–6, and a total RNA SW15731 standard, lane 7.

Referring now to FIG. 7, there is shown a Western blot of MVP levels in a sucrose equilibrium gradient, where lanes 1–6 correspond to the load 20, 30, 40, 45, 50 and 60% layers, respectively, and lane 7 corresponds to GLC/4/ADR P100 fraction layer. Lane M is the Novagent Perfect Protein Marker. Referring now to FIG. 8, there is shown a Northern blot of RNA extracted from gradient fractions of FIG. 7, lanes 1–6, and a total RNA SW1573 standard, lane 7. As can be seen, the majority of MVP and vRNA was present in the 45% layer, coincident with the previously published behavior of purified vault particles, confirming that the increase of MVP and vRNA seen in the P100 fraction accurately reflect the level of assembled vault particles. Therefore, changes in MVP and vRNA levels in the P100 fraction indicates that vault particle levels vary depending on the level of drug susceptibility in the cell lines.

Four additional MDR cell lines were examined, including the parental cell lines and when available, the drug-revertant cell lines. These were SW1573/2R120 and 2R120/rev (non-small cell lung cancer), 8226/MR4 and 8226/MR20 (myeloma cells) and MDF-7/MR.

Referring now to Table I, there is shown a comparison of the P100 fraction MVP and vRNA levels in all six tested drug-resistant and drug-revertant cells lines with levels in their respective parental cell lines, where the fold increase is given as drug-resistant or drug-revertant cell line level divided by parental cell line level.

TABLE I

Increase in the Levels of MPV and vRNA in Drug-Resistant and Drug-Revertant Cell Lines over Parental Cell Lines

| Cell Line | Substance | Fold change |
|---|---|---|
| GLC4/adr | MVP | 15.1 |
|  | vRNA | 13.7 |
| GLC4/rev | MVP | 4.4 |
|  | vRNA | 4.6 |
| SW1573/2R120 | MVP | 2.3 |
|  | vRNA | 3.6 |
| 2R120/rev | MVP | 1.5 |
|  | vRNA | 1.2 |
| S226/MR4 | MVP | 1.5 |
|  | vRNA | 1.5 |
| S226/MR20 | MVP | 1.3 |
|  | vRNA | 1.6 |
| MCF7MR | MVP | 3.7 |
|  | vRNA | 2.9 |

As can be seen, there was as much as a 15- fold increase of MVP levels in resistant/revertant cells line levels over parental cell lines levels and as much as a 13-fold increase of vRNA levels in resistant/revertant cells line levels over parental cell lines levels. The results indicate that increased MVP associated with drug-resistant and drug-revertant cell lines was assembled into a macromolecular form, such as vaults, able to pellet at 100,000×g. Further, as little as 1.3 fold up-regulation of MVP was sufficient to confer the drug resistant phenotype in the 8226/MR20 cell line.

Figure 9:
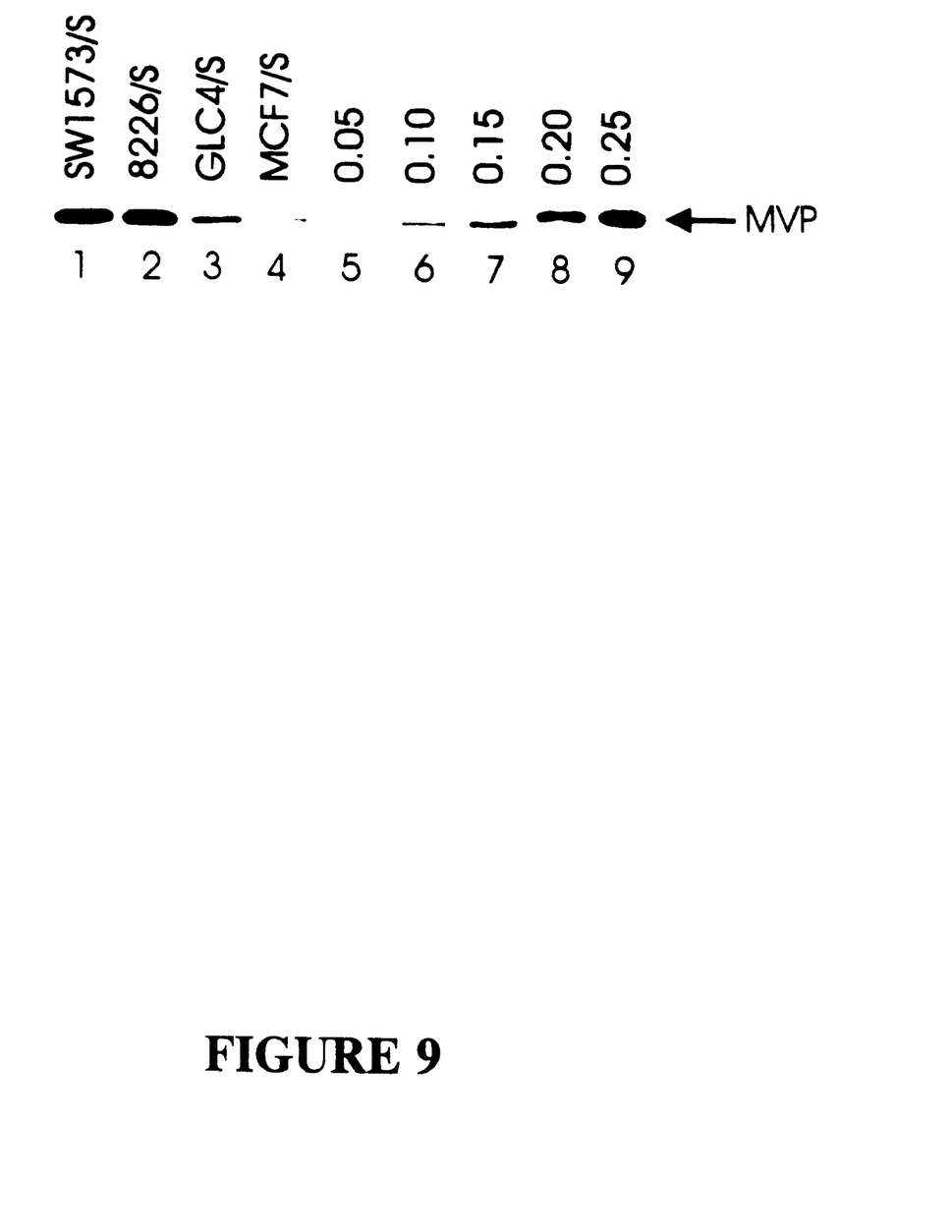
FIG. 9 shows a Western blot of P100 fractions of four parental cell lines, lanes 1–4, and of P100 fractions of purified rat liver vaults, lanes 5–9.

Further, the number of copies of vaults in parental cell lines were determined by analysis of protein levels in the P100 fraction compared with increasing amounts of purified vaults. Referring now to FIG. 9, there is shown a Western blot of P100 fractions of $4 \times 10^3$ cells per lane from the four parental cell lines, lanes 1–4, and of P100 fractions of 0.05–0.25 mg per lane of purified rat liver vaults as indicated, lanes 5–9. The results are summarized in Table II.

TABLE II

Estimation of Number of Copies of Vault Particles

| Cell Line | Cancer Type | Parental × $10^3$ vaults/cell | Drug-resistant × $10^3$ vaults/cell[4] | Revertant × $10^3$ |
|---|---|---|---|---|
| GLC4/S | Small cell lung | 16 = 0.7 | 245 | 71 |
| SW1573 | Non-small cell lung | 37 = 3.9 | 85 | 56 |
| S226/S | Myeloma | 35 = 1.4 | 46 (MR20) | NA |
|  |  |  | 53 (MR4) |  |
| MCF7/S | Breast | 11 = 0.4 | 39 | NA |

As can be seen, vault levels per cell vary considerably among the different cell lines examined and cell lines with lower-levels of endogenous vault particles (GLC4/S and MCF7/S) showed the highest fold induction seen in Table I. Among the cell lines described in Table II, GLC4 and SW1573 were selected with doxorubicin, while 8826/S and MCF7/S were selected with mitoxanthrone. The very high number of vaults in the GLC4 drug-resistant cell line, 245,000 vaults per cell, might reflect the high concentration of doxorubicin to which this line is resistant (1 $\mu$M). This level of doxorubicin is ten times greater that the level used to select the SW1573 resistant lines 0.1 $\mu$M which display only one third the number of vaults per cell. The GLC4 drug-revertant cell line has a reduction in vault number that is still over 4-fold higher than the parent line. However, the GLC4 drug-revertant cell line, although now sensitive to killing by 1 $\mu$M doxorubicin, is still resistant to 0.1 $\mu$M doxorubicin and therefore is more similar to the SW1573 resistant line with regard to drug sensitivity than to the SW1573 drug-revertant line. As can be seen, the vault levels in the GLC4 drug-revertant cell line, 71,000, is similar to the vault level in the SW1573 drug-resistant cell line, 85,000. Thus, the absolute vault levels appear to directly dictate the extent of drug resistance.

D) Methods and Compositions for Treating Multiple Drug-resistant Cancer:

As can be appreciated from the disclosure herein, there is a dynamic relationship between the vRNAs and vaults and there is a pool of vRNAs from which a certain fraction is associated with the vault particle at any particular time. An increase in the general pool of vaults, as in the drug resistant cell lines, results in an increase in the fraction of the vRNAs pool that is vault associated. Further, vault overexpression is a necessary component of the pathway involved in non-Pgp MDR cancer.

vRNAs are not a structural component of the vault particle, as ribonuclease digestion doesn't affect vault particle morphology, but vRNAs appear to have a fundamental role in the function of the vault particle. Hence, one method of disrupting vault function in its role in multidrug resistant cancer is to target the vRNA component.

According to one embodiment of the present invention, there is a method of treating multidrug resistant cancer by disrupting the vRNA component of the vault. In a preferred embodiment, the vRNA component is disrupted by administering antisense oligonucleotides (ODNs), such as phosphorothioate ODNs containing C-5 propyne (C-5P S-ODN)

analogs of uridine and cytidine, in a sufficient quantity to bind the vRNA. Advantageously, these modified ODNs can be used at nanomolar concentrations and are nuclease resistant, but are sensitive to RNAse H activity when hybridized to RNA.

In order to determine the sequence of appropriate antisense oligonucleotides, a series of contiguous antisense ODNs (15–18 bases in length) were synthesized to encompass the entire sequence of hvg1, and the regions of hvg1 that were susceptible to targeted degradation were determined using an antisense ODN-directed RNAse H cleavage assay. Two regions of hvg1 vRNA (H2 and H4) were identified that were susceptible to targeted degradation. In addition, S100 extracts were used to study the pool of non-vault-associated vRNAs and determined that antisense ODN H5 targets all three vRNAs, hvg1, hvg2 and hvg3. Both H2 and H4 C-5P S-ODNs were synthesized and determined to be active in an in vitro RNAse H activity assay (data not shown).

TABLE III

Results of RNase H Cleavage Assay for Various Antisense Nucleotides to hvg1 vRNA

| ODN | Antisense Nucleotides (complementary nucleotides to hgv1) | Deproteinized RNA | P100 RNP | S100 RNP |
|---|---|---|---|---|
| H1 | CCGCTGAGCTAAAGCCAG (3–20) | – | – | – |
| H2 | AAAGAACTGTCGAAGTAA (21–38) | +++ | ++ | +++ |
| H3 | TTGCTTGTTTCAATT (39–53) | – | +/– | +++ |
| H4 | AACCCAGACAGGTTTGC (50–65) | ++ | + | +++ |
| H5 | CCCGCGGGTCTCGAAC (66–81) | – | – | +++ |
| H6 | AAGGACTGGAGAGCG (82–96) | – | – | – |

"+++" = 100% cleavage;
"++" = >50% cleavage;
"+" = 5–50% cleavage;
"+/–" = <5% cleavage;
"–" = no detectable cleavage.

As can be seen, H2 hybridization allowed for RNase H digestion of hvg1 vRNA that was deproteinized (+++), associated with vaults (++) or in the soluble non-vault fraction (+++). Similarly, H3 hybridization allowed for RNase H digestion of hvg1 vRNA that was in the soluble non-vault fraction (+++) and to a small extent associated with vaults (+/–). Additionally, H4 hybridization allowed for RNase H digestion of hvg1 vRNA that was deproteinized (++), in the soluble non-vault fraction (+++) and to some extent associated with vaults (+). Finally, H5 hybridization allowed for RNase H digestion of hvg1 vRNA only in the soluble non-vault fraction (+++).

Additionally, vRNAs in the non-adherent GLC4/ADR cell line were targeted. This line has a 15-fold higher level of vaults than its parent line. An antisense ODN concentration of 100 nM was determined to result in on average about 70% inhibition of vRNAs expression within 24 hours, depending on the ODN type. This resulted in an inhibition of the level of vRNAs of between 50–75% for 3 days in culture as determined by Northern blot analysis, data not shown.

Therefore, according to one embodiment of the present invention, there is provided a purified and isolated polynucleotide molecule consisting essentially of a human vault RNA, or its complementary strands, or a combination of a nucleotide sequence consisting essentially of a human vault RNA and its complementary strands. Further, according to another embodiment of the present invention, there is provided a polynucleotide molecule which hybridizes under stringent conditions to a such a polynucleotide. One example of such stringent conditions is hybridization in 3X SSC, 1X Denhardt's, 25 mM sodium phosphate buffer (pH 7.0), 0.5% SDS, and 2 mM EDTA for 18 hours at 65° C. This hybridization is followed by 3–4 washes in 0.3X SSC, 0.1% SDS for 20 minutes at 65° C.

EXAMPLE I

METHOD OF DIAGNOSING A PATIENT WITH A MULTIDRUG-RESISTANT CANCER

According to one embodiment of the present invention, a patient with a multidrug-resistant cancer is diagnosed by, first, providing a sample of tissue or fluid from the patient. The sample can be bone marrow, cerebral spinal fluid, blood, tears, saliva or a biopsy specimen, or can be other suitable tissue or fluid samples. Next, the level of vault-associated vRNA, such as vault-associated hvg1 vRNA, is determined. Then, the level of the vault-associated vRNA is compared to a known range of levels for the vault-associated vRNA in patients with multidrug-resistant cancers. A diagnosis of multidrug-resistant cancer is made when the level of the vault-associated vRNA determined is within the range of levels for the vault-associated vRNA in patients with multidrug-resistant cancers.

According to another embodiment of the present invention, a patient with a multidrug-resistant cancer is diagnosed by, first, providing a sample of tissue or fluid from the patient. The sample can be bone marrow, cerebral spinal fluid, blood, tears, saliva or a biopsy specimen, or can be other suitable tissue or fluid samples. Next, the level of vaults is determined. Then, the level of the vaults is compared to a known range of levels for the vaults in patients with multidrug-resistant cancers. A diagnosis of multidrug-resistant cancer is made when the level of the vaults determined is within the range of levels for the vaults in patients with multidrug-resistant cancers.

EXAMPLE II

METHOD OF TREATING A PATIENT WITH MULTIDRUG-RESISTANT CANCER

According to another embodiment of the present invention, a patient with a multidrug-resistant cancer is treated by disrupting vaults present in the multidrug-resistant cancer cells making them susceptible to chemotherapy. This is accomplished by administering to the patient at least one antisense polynucleotide having an affinity for a human vRNA. In a preferred embodiment, the antisense polynucleotide binds the human vRNA when it is vault associated. In a particularly preferred embodiment, the antisense polynucleotide is selected from the group consisting of a polynucleotide that has a sequence complimentary to residues 21–38 of SEQ ID NO:1, a polynucleotide that has a sequence complimentary to residues 39–53 of SEQ ID NO:1, a polynucleotide that has a sequence complimentary to residues 50–65 of SEQ ID NO:1 and a combination of the foregoing. The method can also include administering to the patient an RNase capable of digesting the hybridized vRNA. However, suitable RNases exist within the cells which will degrade the hybridized vRNA.

EXAMPLE III
COMPOSITION FOR TREATING A PATIENT WITH MULTIDRUG-RESISTANT CANCER

According to another embodiment of the present invention, there is provided a composition for treating a patient with a multidrug-resistant cancer. The composition comprises at least one antisense polynucleotide having an affinity for a human vRNA. In a preferred embodiment, the antisense polynucleotide binds the human vRNA when it is vault associated. In a particularly preferred embodiment, the antisense polynucleotide is selected from the group consisting of an RNA polynucleotide that has a sequence corresponding to residues 21–38 of SEQ ID NO:1, an RNA polynucleotide that has a sequence corresponding to residues 39–53 of SEQ ID NO:1, an RNA polynucleotide that has a sequence corresponding to residues 50–65 of SEQ ID NO:1 and a combination of the foregoing. The composition can additionally include a suitable carrier and other appropriate substances as will be understood by those with skill in the art with reference to the disclosure herein.

EXAMPLE IV
METHOD OF SCREENING FOR COMPOSITIONS FOR TREATING A PATIENT WITH MULTIDRUG-RESISTANT CANCER

According to one embodiment of the present invention, there is provided a method of screening for compositions for treating a patient with multidrug-resistant cancer. The method includes determining compositions or treatments that disrupt the association of vRNA with vault particles. In a preferred embodiment, the method includes determining compositions or treatments that disrupt the association of vRNA with the minor vault proteins of vault particles.

Although the present invention has been discussed in considerable detail with reference to certain preferred embodiments, other embodiments are possible. Therefore, the spirit and scope of the appended claims should not be limited to the description of preferred embodiments contained in this application.

SEQUENCE LISTING

<160> NUMBER OF SEQ ID NOS: 4

<210> SEQ ID NO 1
<211> LENGTH: 98
<212> TYPE: DNA
<213> ORGANISM: Homo sapiens

<400> SEQUENCE: 1
ggctggcttt agctcagcgg ttacttcgac agttctttaa ttgaaacaag caacctgtct      60
gggttgttcg agacccgcgg gcgctctcca gtcctttt      98

<210> SEQ ID NO 2
<211> LENGTH: 88
<212> TYPE: DNA
<213> ORGANISM: Homo sapiens

<400> SEQUENCE: 2
ggctggcttt agctcagcgg ttacttcgag tacattgtaa ccacctctct gggtggttcg      60
agacccgcgg gtgctttcca gctctttt      88

<210> SEQ ID NO 3
<211> LENGTH: 88
<212> TYPE: DNA
<213> ORGANISM: Homo sapiens

<400> SEQUENCE: 3
ggctggcttt agctcagcgg ttacttcgcg tgtcatcaaa ccacctctct gggttgttcg      60
agacccgcgg gcgctctcca gccctctt      88

<210> SEQ ID NO 4
<211> LENGTH: 101
<212> TYPE: DNA
<213> ORGANISM: Homo sapiens

<400> SEQUENCE: 4
ggctggcttt agctcagcgg ttacttcgac aatgctttcc atggttagga aaccaacctc      60
tctgggtggt ttgagacccg tgggccctct ccagtcecttt t      101

We claim:

1. An isolated polynucleotide encoding a human vault-associated vRNA or its complementary strand.

2. The polynucleotide of claim 1, having a sequence as set forth in SEQ ID NO:1.

3. The polynucleotide of claim 1, having a sequence as set forth in SEQ ID NO:2.

4. The polynucleotide of claim 1, having a sequence as set forth in SEQ ID NO:3.

5. An isolated polynucleotide molecule having a sequence as set forth in SEQ ID NO:1, or its complementary strands.

6. A isolated polynucleotide molecule having a sequence as set forth in SEQ ID NO:2, or its complementary strands.

7. An isolated polynucleotide molecule having a sequence as set forth in SEQ ID NO:3, or its complementary strands.

8. An isolated polynucleotide molecule having a sequence as set forth in SEQ ID NO:4, or its complementary strands.

9. A composition consisting essentially of a purified human vault RNA, or its complementary strands, or a combination of a human vault RNA and its complementary strands.

10. A polynucleotide molecule which hybridizes under stringent conditions to a polynucleotide sequence according to claim 1, or its complementary strands.

11. A vector containing the polynucleotide of claim 1.

12. A prokaryotic or eukaryotic host cell stably transformed or transfected by the vector of claim 11.

13. A method of diagnosing a patient with a multidrug-resistant cancer comprising:

(a) providing a sample of tissue or fluid from the patient;

(b) determining the level of a human vault-associated vRNA in the patient sample; and (c) comparing the level of the human vault-associated vRNA determined in step (b) to a known range of levels for the human vault-associated vRNA in patients with multidrug-resistant cancers, wherein a diagnosis of multidrug-resistant cancer is made when the level of the human vault-associated vRNA determined in step (b) is within the range of levels for the human vault-associated vRNA in patients with multidrug-resistant cancers.

14. The method of claim 13, wherein the sample is selected from the group consisting of bone marrow, cerebral spinal fluid, blood, tears, saliva and a biopsy specimen.

15. A method of screening for compositions or treatments for treating a patient with multidrug-resistant cancer, comprising determining compositions or treatments that disrupt the association of vRNA with vault particles.

16. A method of screening for compositions or treatments for treating a patient with multidrug-resistant cancer, comprising determining compositions or treatments that disrupt the association of vRNA with the minor vault proteins of vault particles.

17. A purified polynucleotide encoding a human vault-associated vRNA or its complementary strand.

18. The polynucleotide of claim 17, having a sequence as set forth in SEQ ID NO:1.

19. The polynucleotide of claim 17, having a sequence as set forth in SEQ ID NO:2.

20. The polynucleotide of claim 17, having a sequence as set forth in SEQ ID NO:3.

* * * * *